United States Patent [19]

Dove et al.

[11] Patent Number: 4,684,723

[45] Date of Patent: Aug. 4, 1987

[54] METHOD OF SEPARATING PROTEINS FROM AQUEOUS SOLUTIONS

[75] Inventors: George B. Dove, Hercules; Gautam Mitra, Kensington, both of Calif.

[73] Assignee: Miles Laboratories, Inc., Elkhart, Ind.

[21] Appl. No.: 774,677

[22] Filed: Sep. 11, 1985

[51] Int. Cl.[4] ............................................. C07G 7/00
[52] U.S. Cl. .................................. 530/351; 530/364; 530/380; 530/386; 530/389; 530/395; 530/420; 530/421; 210/656; 210/905; 210/927; 424/101
[58] Field of Search ............... 530/350, 351, 358, 364, 530/380, 386, 389, 395, 420, 421; 260/112 B, 112 R; 210/656, 927, 905; 424/101

[56] References Cited

U.S. PATENT DOCUMENTS 3,415,804 12/1968 Polson ..................................... 424/88
3,790,552  2/1974 Johnson et al. ...................... 210/927
4,439,358  3/1984 Coan et al. ........................... 424/101

Primary Examiner—John Kight
Assistant Examiner—Nathan M. Nutter
Attorney, Agent, or Firm—Pamela A. Simonton; Lester E. Johnson

[57] ABSTRACT

There is disclosed an improved method for separating and recovering proteins, particularly therapeutically active proteins, from an aqueous system also containing a component having the ability to create two liquid phases by use of salt partitioning technology. By the addition of water soluble inorganic salts to an aqueous system containing one or more therapeutically active proteins or nucleic acids, especially an aqueous system obtained from fractionation of a blood plasma fraction or from a tissue culture fluid resulting from a biotechnology production operation such as recombinant DNA and monoclonal antibody technologies, the aqueous system may be separated into two or more liquid phases. Such separated phases may be selectively enriched in components of the original aqueous system having differing solubility in the so-separated liquid phases.

6 Claims, 1 Drawing Figure

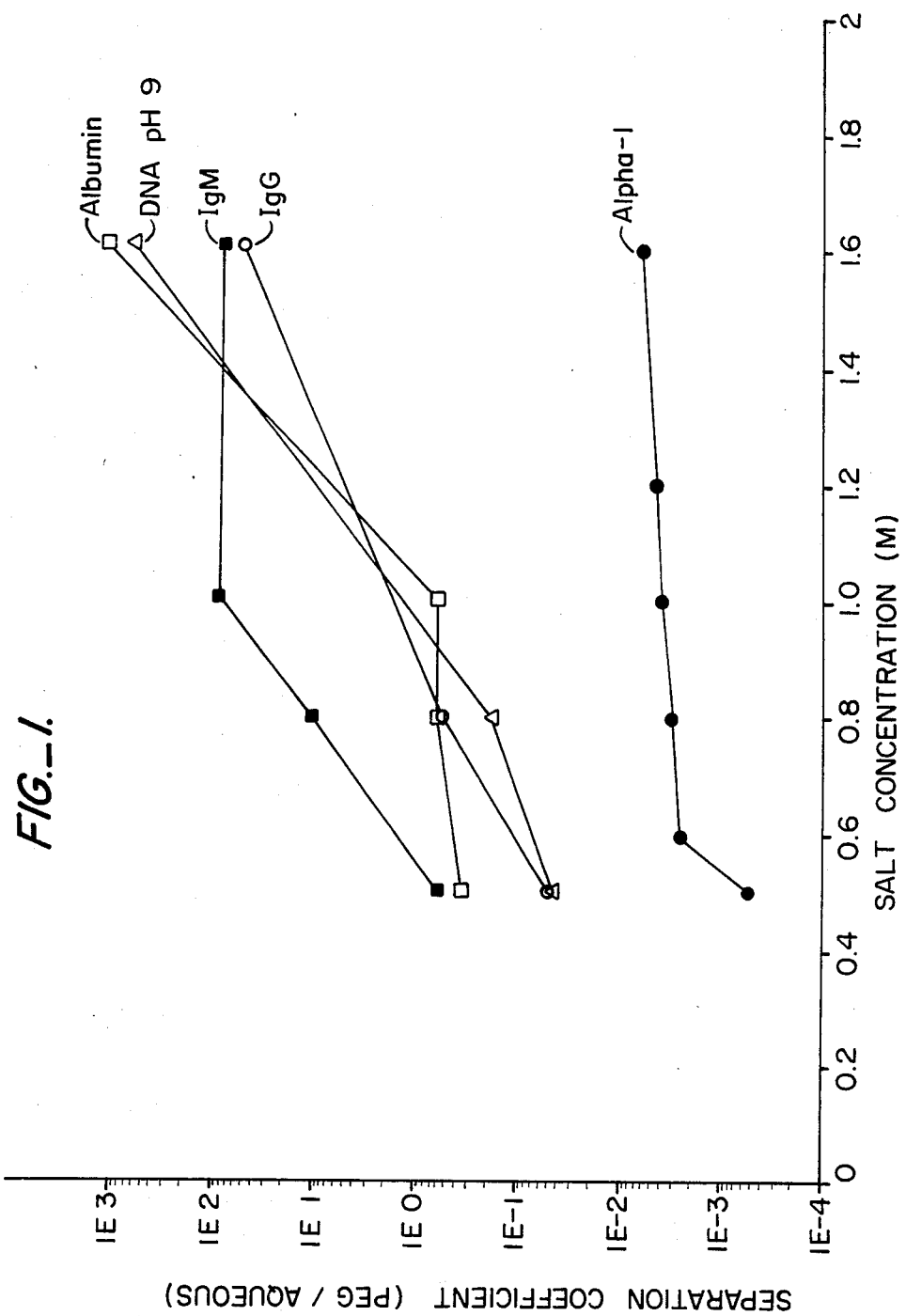
FIG._1.

METHOD OF SEPARATING PROTEINS FROM AQUEOUS SOLUTIONS

BACKGROUND OF THE INVENTION

1. Field of the Invention

This invention relates to, and has as its object, an improved method for separating therapeutically active proteins and nucleic acids from an aqueous system such as, for example, blood plasma or a fraction thereof and tissue culture fluids obtained using biotechnology production processes, by use of salt partitioning technology.

2. Description of the Prior Art

Blood plasma has been fractioned by well known methods to separate therapeutically active proteins therefrom, for example, by the Cohn Fractionation Method disclosed in E. J. Cohn et al, *J. Amer. Chem. Soc.*, 68, 459 (1946) and Cohn, U.S. Pat. No. 2,390,074.

Among such therapeutically active proteins which may be isolated and recovered from blood plasma or fractions thereof, there may be mentioned alpha-1 antitrypsin (also referred to as alpha-1-proteinase inhibitor and abbreviated as "PI"), immunoglobulins and human serum albumin.

Alpha-1-proteinase inhibitor has been isolated from blood plasma by a number of methods as reported by Pannell et al, *Biochemistry*, 13, 5439 (1974); Saklatvala et al, *Biochem. J.*, 157 339 (1976); Musiani et al, *Biochem.*, 15, 798 (1976); Kress et al, *Preparative Biochemistry*, 3 (6), 541 (1973); Glaser et al, ibid, 5 (4), 333 (1975); Hao et al, *Proceedings of the International Workshop on Technology for Protein Separation and Improvement of Blood Plasma Fractionation*, held Sept. 7–9, 1977, Reston, Va.; and Coan and Brockway, U.S. Pat. Nos. 4,379,087 and 4,439,358. According to the conventional methods of isolating PI, plasma has first been fractionated using known precipitants such as ammonium sulfate and polyethylene glycol and cold ethanol. The resulting fraction(s) containing PI for example, Cohn Fr. IV, IV-1, and Effl. II+III, are then subjected to one or more chromatographic separation steps to remove unwanted proteins. Although the known methods are useful to isolate PI, such methods have disadvantages including lowered yields due to denaturation resulting from harsh physical conditions such as temperature and pH employed, chemical denaturation due to the precipitants used, incomplete separation of unwanted proteins in the chromatographic separation steps, and incomplete recovery from the final precipitate and solutions thereof obtained in the known methods.

Immunoglobulins have been isolated from blood plasma by a number of known methods including the Cohn Fractionation Method mentioned above. In addition to the above, intravenously injectable immune serum globulin, which comprises predominantly IgG immunoglobulins, may be obtained as disclosed by Tenold, U.S. Pat. Nos. 4,396,608 and 4,499,073. Immunoglobulin M may be produced by a modification of tissue culture technology.

Human serum albumin may be isolated from blood plasma by methods such as those disclosed by Schneider et al, U.S. Pat. No. 4,156,681; Ivanov et al, U.S. Pat. No. 3,926,939; Schuck et al, U.S. Pat. No. 4,075,197; Hansen et al, U.S. Pat. No. 4,177,188; Plan et al, U.S. Pat. No. 3,992,367; and Hink, U.S. Pat. No. 2,958,628.

Nucleic acids, for example DNA, can be isolated from animal tissue or produced by r-DNA technology using known methods.

The known methods for the isolation and recovery of immunoglobulins, human serum albumin, and nucleic acids all have disadvantages similar to those mentioned above in regards to PI.

SUMMARY OF THE INVENTION

This invention is a method for separating at least one member of the group consisting of therapeutically active proteins and nucleic acids from an aqueous system containing (1) at least one of said member of the group consisting of therapeutically active proteins and nucleic acids, and (2) at least one polymer component that is at least partly water-miscible and has the ability to create two liquid phases in said aqueous system selected from the group consisting of polyalkylene glycols, a polymer having a cellulosic backbone and polymer having a polyacrylamide backbone, which method comprises adding to said aqueous system an amount of water soluble, inorganic salt sufficient to separate said aqueous system into two liquid phases, one of said two liquid phases containing a major amount of at least one of said member of the group of therapeutically active proteins and nucleic acids.

BRIEF DESCRIPTION OF THE DRAWING

FIG. 1 shows a summation of separation coefficents as a function of salt concentration for DNA, alpha-1-Proteinase Inhibitor, Albumin, Immunoglobulin M and Immunoglobulin G.

DESCRIPTION OF THE PREFERRED EMBODIMENT

According to the method of this invention, the aqueous system containing the therapeutically active protein and/or nucleic acid material is selected from blood plasma, a blood plasma fraction dissolved in water, a blood plasma protein concentrate dissolved in water, and a tissue culture fluid (also referred to as a "tissue culture broth" or "broth") obtained using a biotechnology production process. The method has been found to be especially useful when applied to aqueous systems containing at least one of alpha-1 antitrypsin (alpha-1-proteinase inhibitor, or "PI"); immunoglobulins, especially, immunoglobulin G and immunoglobulin M ("IgG" and "IgM", respectively); human serum albumin; and nucleic acids, such as DNA; whether obtained from blood plasma or tissue (human tissue) sources or by biotechnology production processes including recombinant-DNA (r-DNA) technology, or antibody or monoclonal antibody technology and the like.

The polymer component should be at least partly miscible in water and possess hydrophobic-hydrophilic properties that, when it is added to the aqueous system, will create two liquid phases, for example, one phase rich in the polymer component and the other rich in the added salt. As the polymer component, there may be used a polyalkylene glycol such as polyethylene glycol and polypropylene glycol or a polymer having a cellulosic, or, broadly, a carbohydrate backbone such as dextran, or a polymer having a polyacrylamide backbone where the amino moiety of the basic acrylamide monomer may be substituted with any well known substituent which will alter the hydrophobic-hydrophilic properties of the polyacrylamide. Preferably, the polymer component is polyethylene glycol (PEG). The polyethylene glycol may have a molecular weight in the range of about 200 to 20,000, preferably about 2,000–10,000, more preferably about 3,000 to 8,000, most preferably about 3,000 to 4,000.

The water-soluble salt, broadly, may be any water-soluble inorganic or organic salt, preferably a water-soluble inorganic salt, more preferably a water-soluble inorganic salt selected from the group consisting of potassium phosphate, dibasic; ammonium sulfate, dibasic; sodium phosphate, dibasic; and sodium sulfite dibasic. Most preferably, the salt is selected from potassium phosphate, dibasic and ammonium sulfate, dibasic. Preferably, the salt is used at a concentration of about 0.5–2.0 M, more preferably about 0.5–1.6 M, most preferably about 0.8–1.0 M.

Generally, it is especially preferred that the aqueous system contain, in addition to the protein or nucleic acid, at least PEG and optionally a polymer such as dextran or a polyacrylamide and that water-soluble, inorganic salt be added thereto.

Parameters for controlling the amount of PEG and protein in the two phases which separate include the amount of PEG (or dextran), the salt, salt concentration, temperature, pH and volume size, although volume size may not be critical.

PEG is used preferably in the range of about 10–30% (w/v), more preferably about 15–25% (w/v), most preferably about 10–20% (w/v).

When the cellulosic polymer, such as dextran, or polyacrylamide is used, it may be used in the range of about 5–20% (w/v), more preferably about 5–15% (w/v), most preferably about 5–10% (w/v).

The temperature of the mixture formed in the practice of the method according to this invention may be in the range of about $(-)5°$ C. to about $100°$ C., preferably about $(-)5°$ C. to about $50°$ C., more preferably about $(-)5°$ C. to about $20°$ C., most preferably about $(-)5°$ C. to about $5°$ C.

The pH of the mixture formed in the practice of the method according to this invention preferably may be in the range of about 4 to 11, more preferably about 5 to 9, most preferably about 7–9.

It has been observed that specific proteins, for example, alpha-1 antitrypsin, exhibit low separation coefficients (S.C.=amount in PEG phase/amount in water phase) in a wide range of conditions. Higher salt concentration and higher pH lead to higher separation coefficients as defined above. The S.C. of PI is 0.0025 at 0.6 M salt concentration and it increases to 0.0062 at 1.6 M salt. Generally, proteins exhibit a S.C. of about 0.01 to 100. The PEG S.C. increases to about 200 or greater in 1.0 M salt concentration. Altering the pH to make proteins or other partitioned materials more or less hydrophilic induces greater or lower water solubility. A pH in the range of 5–9 increases the S.C. generally about 100-fold or greater. And, further, the trends demonstrated by salt concentration done are amplified. Lower temperatures increase the PEG S.C. by about 2- to 1-fold with little change in the protein S.C.

The spontaneous appearance of two or more liquid phases in a system occurs when sufficient insolubility exists between two components. In an aqueous system consisting of polyethylene glycol (PEG) and a salt (e.g. dipotassium phosphate), the upper phase is enriched in PEG and the lower phase in salt Parameters that may be altered include:
(a) Chemical basis and molecular weight of primary polymer (e.g. PEG).
(b) Chemical basis of second additive (e.g. polymer, salt).
(c) Concentrations of additives.
(d) pH.
(e) Temperature.

The use of partitioned phases has several advantages over other widely used methods of separation. (1) Physical and chemical parameters may be controlled to minimize denaturation. Simple mixing only is required; centrifugation may be used to hasten separation. Shear is virtually eliminated. Appropriate choices of polymers and salts reduce exposure to denaturing agents. (2) Conditions may be tailored to specific isolation requirements, offering a basis of separation (involving chemical affinities and solubilities based on pH and the presence of salts) unavailable with other techniques. (3) The process is easily scaled to any volume of material, with minimal capital investment.

Beyond conventional products, the methodology is applicable to biotechnical separations with unique possibilities. The partitioning of phases allows components to be separated within the confines of another operation. Production of a material (e.g. fermentation and subsequent cell separation) may be simplified. In a PEG/dextran system, cells and cellular components partition to the bottom phase, leaving the top phase available for product. Alpha amylase has been partitioned to the top phase and Bacillus subtilis cells to the bottom phase. Production of biologically active materials may be enhanced by removal of product from cells or cellular components for two reasons: (1) Degradation of product by extra- or intra-cellular enzymes still present in the broth is prevented, (2) Removal of product reduces negative feedback inhibition of growth or production of cells. The method is unique in speed and ease for handling bulk quantities which is critical for sensitive systems.

The use of the method according to the present invention for separating proteins or nucleic acids from aqueous systems containing the same is especially useful in tissue culture fluids to disrupt the cell whereby the desired protein and intracellular product(s) along with the degrading enzymes are released. By use of the method according to this invention, the aqueous tissue culture fluid can be partitioned to achieve a fast bulk separation of the material produced by biotechnology production processes from cellular components and degrading enzymes.

Materials/Methods: Polyethylene glycol (PEG 3350) was obtained from Union Carbide. PEG 3350 has a molecular weight of 3300–3400. Reagents (potassium phosphate dibasic, phosphoric acid) were obtained from J. T. Baker, "Baker analyzed" reagent grade. Systems were equilibrated in Falcon polypropylene centrifuge tubes.

Simple systems (with defined components) were designed with the following materials. Calf thymus DNA, polymerized, was obtained from Sigma. Protein sources were prepared in-house and subsequently dialyzed into low salt solutions. Human serum albumin and immunoglobulin G (IgG) were plasma-derived. Human immunoglobulin M (IgM) was produced by tissue culture and purified. A complex system (undefined) was set up with an intermediate material of Cohn plasma fractionation containing alpha-1 antitrypsin (alpha-1) and albumin.

In the simple systems, PEG/salt systems with 20% w/v PEG and appropriate salt were mixed vigorously and adjusted to pH with phosphoric acid. Protein concentrates in unbuffered solutions were added to a concentration of 10 mg/ml. In the complex systems, PEG and salt were added to the plasma fraction. Systems were gently mixed by rocking at defined temperatures. The mixtures were allowed to settle overnight and were centrifuged at 2000RCF.

Samples were assayed by absorbance at 280 nm, Bradford protein assay, and radial immunodiffusion plates (Helena Laboratories). DNA was assayed by the methods of Burton and Giles and Myers, with modifications.

In a method for separation alpha-1-proteninase inhibitor from an aqueous solution containing the same, which comprises the steps of (a) holding the aqueous solution containing alpha-1-proteinase inhibitor at a pH of about 6.5–8.5, and a temperature of about 2°–50° C. for a period of about 0.2–24 hours, (b) mixing the solution from step (a) with from about 8% to about 23% (weight/volume) of a polyalkylene glycol, based on the volume of aqueous solution containing the alpha-1-proteinase inhibitor and adjusting the pH of the mixture from about 4.6 to about 7.5 for a time and at a temperature sufficient to selectively precipitate unwanted proteins from the mixture without precipitation of alpha-1-proteinase inhibitor wherein the amount of polyalkylene glycol used may vary 8% to 10% at about pH 4.6 to from about 20% to 23% at pH 7.5 and may be incrementally increased in the range of about 2% to about 3% per 0.5 increase in pH, and (c) separating alpha-1-proteinase inhibitor from the solution from step (b), the improvement comprising separating alpha-1-proteinase inhibitor from said mixture by salt partition techniques by the addition to said mixture of from about 0.5 M to about 1.6 M of at least one water soluble, inorganic salt at a temperature of from about $(-)52^0$ C. to about 5° C. and at a pH of from about 5 to about 9 to obtain an aqueous solution containing alpha-1-proteinase inhibitor free of unwanted proteins.

Results

Relative volumes between the two phases changes as the salt concentration increases or other parameters are altered. In general, the volume ratio (PEG/aqueous) decreases as the salt concentration or plot increases. Perturbation of components or concentration of components (e.g. adjustment of pH with phosphoric or other acid results in larger changes. For example, adjustment of pH with hydrochloric acid prevents an interface from forming below pH 5.5.

DNA, albumin, IgG, IgM and alpha-1 follow similar trends. Results with albumin are less consistent than with other materials. As the salt concentration increases, the concentration of material in the aqueous phase decreases and the separation coefficient increases. The same pattern is exhibited with increasing pH. Further, the trends appear to be somewhat additive: increasing the salt concentration and pH lead to the greatest separation coefficients. Temperature changes give mixed results with little change.

A summation of separation coefficients at pH 9 is given in the attached Figure. The relative values are similar with the exception of alpha-1. The low values of alpha-1 (range of 0.002–0.006) increase with salt and pH, but demonstrate a much greater affinity for the aqueous phase. The difference between alpha-1 and other proteins may be attributed to either the intrinsic nature of alpha-1 (e.g. low hydrophobicity) or the presence of contaminants in the aqueous phase attracting alpha-1 or in the PEG phase repelling alpha-1.

What is claimed is:

1. A method for separating alpha-1-proteninase inhibitor from a group consisting of therapeutically active proteins and nucleic acids in an aqueous system containing (1) at least one of said member of the group consisting of therapeutically active proteins and nucleic acids, and (2) at least one polymer component that is at least partly water-miscible and has the ability to create two liquid phases in said aqueous system selected from the group consisting of polyalkylene glycols, a polymer having a cellulosic backbone and a polymer having a polyacrylamide backbone, which method comprises adding to said aqueous system an amount of at least one water soluble, inorganic salt sufficient to separate said aqueous system into two liquid phases, the improvement comprising separating alpha-1-proteinase inhibitor from said mixture by salt partition techniques to form a salt phase and a polyalkylene glycol phase by the addition to said mixture of from about 0.5 M to about 1.6 M of at least one water soluble, inorganic salt at a temperature of from about $(-)5°$ C. to about 5° C. and at a pH of from about 5 to about 9 to obtain an aqueous solution containing alpha-1-proteinase inhibitor in said salt phase free of unwanted proteins and substantially free of polymer.

2. A method according to claim 1 wherein said aqueous system is selected from blood plasma, a blood plasma fraction dissolved in water, a blood plasma protein concentrate dissolved in water, and a tissue culture fluid obtained using a biotechnology production process.

3. A method according to claim 1 wherein said therapeutically active protein is a member of the group consisting of alpha-1 antitrypsin, immunoglobulins, and human serum albumin and wherein said nucleic acid is a DNA.

4. A method according to claim 1 wherein said salt is a water soluble, inorganic salt is at least one member selected from the group consisting of (1) potassium phosphate, dibasic; (2) ammonium sulfate, dibasic; (3) sodium phosphate, dibasic; and (4) sodium sulfite, dibasic.

5. A method according to claim 1 wherein said polymer component is selected from the group of polyalkylene glycols including polyethylene glycol and polypropylene glycol and said cellulosic backbone polymer dextran.

6. In a method for separation alpha-1-proteninase inhibitor from an aqueous solution containing the same, which comprises the steps of (a) holding the aqueous solution containing alpha-1-proteinase inhibitor at a pH of about 6.5–8.5, and a temperature of abut 2°–50° C. for a period of about 0.2–24 hours, (b) mixing the solution form step (a) with from about 8% to about 23% (weight/volume) of a polyalkylene glycol, based on the volume of aqueous solution containing the alpha-1-proteinase inhibitor and adjusting the pH of the mixture from about 4.6 to about 7.5 for a time and at a temperature sufficient to selectively precipitate unwanted proteins from the mixture without precipitation of alpha-1-proteinase inhibitor wherein the amount of polyalkylene glycol used may vary 8% to 10% at about pH 4.6 to from about 20% to 23% at pH 7.5 and may be incrementally increased in the range of about 2% to about 3% per 0.5 increase in pH, and (c) separating alpha-1-proteinase inhibitor from the solution from step (b), the improvement comprising separating alpha-1-proteinase inhibitor from said mixture by salt partition techniques to form a salt phase and a polyalkylene glycol phase by the addition to said mixture of from about 0.5 M to about 1.6 M of at least one water soluble, inorganic salt at a temperature of from about $(-)5°$ C. to about $5°$ C. and at a pH of from about 5 to about 9 to obtain an aqueous solution containing alpha-1-proteinase inhibitor in said salt phase free of unwanted proteins and substantially free of polyalkylene glycol.

* * * * *